US005744476A

United States Patent [19]
Locke et al.

[11] Patent Number: 5,744,476
[45] Date of Patent: Apr. 28, 1998

[54] DOPAMINE $D_1$ AGONISTS FOR THE TREATMENT OF DEMENTIA

[75] Inventors: Kenneth Walter Locke, Littleton; Thomas David Steele, Acton, both of Mass.

[73] Assignee: Interneuron Pharmaceuticals, Inc., Lexington, Mass.

[21] Appl. No.: 266,816

[22] Filed: Jun. 27, 1994

[51] Int. Cl.$^6$ .................................................. A61K 31/435
[52] U.S. Cl. ........................... 514/284; 514/212; 514/281
[58] Field of Search ............................... 514/284, 212, 514/281; 546/61, 43; 540/595

[56] References Cited

U.S. PATENT DOCUMENTS

| | | |
|---|---|---|
| 4,785,014 | 11/1988 | Goldman-Rakic et al. ............ 514/401 |
| 4,847,300 | 7/1989 | Arnsten et al. ....................... 514/617 |
| 5,047,536 | 9/1991 | Nichols ................................. 546/61 |
| 5,300,642 | 4/1994 | Earl et al. ............................. 544/238 |
| 5,420,134 | 5/1995 | Nichols ................................. 514/280 |

OTHER PUBLICATIONS

Arnsten et al., Nov. 7–12, 1993, "Dopamine $D_1$ Agonists Improve Spatial Working Memory Performance In Monkeys," *Society For Neuroscience Abstracts*, vol. 19, Part 1, p. 367, No. 1 153.1.

Arnsten et al., Oct. 1994, "Dopamine $D_1$ receptor mechanisms in the cognitive performance of young adult and aged monkeys," *Psychopharmacology*, 116(2):143–151.

Schneider et al., Brain Research, vol. 663, pp. 140–144, 1994.

Acquas, E. et al., 1994, "The Potent and Selective Dopamine $D_1$ Receptor Agonist A–77636 Increases Cortical and Hippocampal Acetylcholine Release in the Rat", Eur. J. Pharmacol. 260:85–87.

Archer, T. et al., 1988, "Neonatal 6–Hydroxydopamine–Induced Dopamine Depletions: Motor Activity and Performance in Maze Learning", Pharmacol. Biochem. Behav. 31:357–364.

Arendt, T. et al, 1985, "Nueronal Loss in Different Parts of the Nucleus Basalis is Related to Neuritis Plaque formation in Cortical Target Areas in Alzheimer's Disease", Neurosci., 14:1–14.

Bartus, R. et al., 1985, "Selective Memory Loss Following Nucleus Basalis Lesions: Long Term Behavioral Recovery Despite Persistent Cholinergic Deficiencies", Pharmacol. Biochem. Behav. 23:125–135.

Bertorelli, R. and Consolo, S., 1990, "$D_1$ and $D_2$ Dopaminergic Regulation of Acetylcholine Release from Striata of Freely Moving Rats", J. Neurochem. 54:2145–2148.

Bianchine, J., 1985, "Drugs for Parkinson's Disease, Spasticity. and Acute Muscle Spams", In: *The Pharmacological Basis of Therapeutics*, ed.: Gilman et al., pp. 473–490, Macmillan Publishing Co., New York.

Brewster, W. et al., 1990, "trans–10,11–Dihydroxy–5,6,6a, 7,8,12b–hexahydrobenzo[a]phenanthridine: A Highly Potent Selective Dopamine $D_1$ Full Agonist" J. Med. Chem. 33:1756–1764.

Brown, R. and Marsden, C., 1984, "How Common is Dementia in Parkinson's Disease?", Lancet ii:1262–1265.

Brozoski, T. et al., 1979, "Cognitive Deficit Caused by Regional Depletion of Dopamine in Prefrontal Cortex of Rhesus Monkey", Science 205:929–932.

Caine, D., 1978, "Parkinsonism—Clinical and Neuropharmacological Aspects", Postgrad. Med. 64:82–88.

Castellano, C. et al., 1991, "Post–Training Dopamine Receptor Agonists and Antagonists Affect Memory Storage in Mice Irrespective of Their Selectivity for D1 or D2 Receptors", Behav. Neural. Biol. 56:283–291.

Colombo, P. et al., 1989, "Allocentric Spatial and Tactile Memory Impairments in Rats With Dorsal Caudate Lesions Are Affected by Preoperative Behavioral Training", Behav. Neurosci. 103:1242–1250.

Creese, I., 1987, "Biochemical Properties of CNS Dopamine Receptors", In: *Psychopharmacology: The Third Generation of Progress*, ed.:H. Meltzer, pp. 257–264, Raven Press, New York.

Cummings, J., 1988, "The Dementias of Parkinson's Disease: Prevalence, Characteristics, Neurobiology, and Comparison with Dementia of the Alzheimer Type", Eur. Neurol. 28 (suppl. 1):15–23.

Curtis, L. et al., 1984, "Effect of L–Dopa on Course of Parkinson's Disease", Lancet ii:211–212.

Damsma, G. et al., 1990, "Dopaminergic Regulation of Striatal Cholinergic Interneurons: An In Vivo Microdialysis Study", Arch. Pharmacol. 342:523–527.

Damsma, G. et al., 1990, "Dopamine $D_1$ Receptor Stimulation Increases Striatal Acetylcholine Release in the Rat", Eur. J. Pharmacol. 186:335–338.

Darney, K. et al., 1991, "Behavioral Effects in the Rat of Dihydrexidine, a High–Potency, Full–Efficacy $D_1$ Dopamine Receptor Agonist", Neuropsychopharmacol. 5:187–195.

Davidson, M. et al., 1991, "Cholinergic Strategies in the Treatment of Alzheimer's Disease", Acta Psychiatr. Scand. (suppl. 366):47–51.

Day, J. and Fibiger, H., 1993, "Dopaminergic Regulation of Cortical Acetylcholine Release: Effects of Dopamine Receptor Agonists", Neurosci. 54:643–648.

Dubois, B. et al., 1985, "Profound Disturbances of Spontaneous and Learned Behaviors Following Lesions of the Nucleus Basalis Magnocellularis in the Rat", Brain Res. 338:249–258.

(List continued on next page.)

*Primary Examiner*—Richard L. Raymond
*Attorney, Agent, or Firm*—Pennie & Edmonds

[57] ABSTRACT

This invention provides for a method of raising extracellular brain acetylcholine levels to improve cognition by the administration to a warm-blooded animal of a pharmaceutical composition comprising an effective amount of a dopamine $D_1$ agonist.

18 Claims, 7 Drawing Sheets

OTHER PUBLICATIONS

Dubois, B. et al., 1992, "Deterioration of Dopaminergic Pathways and Alterations in Cognition and Motor Functions", J. Neurol. 239 (suppl. 1):S9–S12.

Dunnett, S., 1985, "Comparative Effects of Cholinergic Drugs and Lesions of Nucleus Basalis or Fimbria–Fornix Delayed Matching in Rats", Psychopharmacol. 87:357–363.

Girotti, F. et al., 1988, "Dementia and Cognitive Impairment in Parkinson's Disease", J. Neurol. Neurosurg. Psych. 51:1498–1502.

Goetz, C., 1990, "Dopaminergic Agonists in the Treatment of Parkinson's Disease", Neurology 40 (suppl. 3):50–57.

Imperato, A. et al., 1993, "Stimulation of Both Dopamine $D_1$ and $D_2$ Receptors Facilitates In Vivo Acetylcholine Release in the Hippocampus", Brain Res. 618:341–345.

Iorio, L. et al., 1983, "SCH 23390, a Potential Benzazepine Antipsychotic with Unique Interactions on Dopaminergic Systems", J. Pharmacol. Exp. Ther. 226:462–468.

Kirkby, R. and Polgar, S., 1974, "Active Avoidance in the Laboratory Rat Following Lesions of the Dorsal or Ventral Caudate Nucleus", Physiol. Psychol. 2:301–306.

Kish, S. et al., 1988, "Uneven Pattern of Dopamine Loss in the Striatum of Patients with Idiopathic Parkinson's Disease", New Eng. J. Med. 318:876–880.

Koller, W., 1989, "Diagnosis and Treatment of Parkinson's Disease", Mod. Med. 57:114–129.

Lees, A., 1985. "Parkinson's Disease and Dementia", Lancet i:43–44.

Levin, E. and Rose, J., 1991, "Interactive Effects of $D_1$ and $D_2$ Agonists with Scopolamine on Radial–Arm Maze Performance", Pharmacol. Biochem. Behav. 38:243–246.

Lovenberg, T. et al., 1989, "Dihydrexidine, a Novel Selective High Potency Full Dopamine D–1 Receptor Agonist", Eur. J. Pharmacol. 166:111–113.

Major, R. and White, N., 1978, "Memory Facilitation by Self–Stimulation Reinforcement Mediated by the Nigro–Neostriatal Bundle", Physiol. Behav. 20:723–733.

McGaugh, J., 1966, "Time–Dependent Processes in Memory Storage", Science 153:1351–1358.

McGurk, S. et al., 1992, "Dopaminergic Drugs Reverse the Impairment of Radial Arm Maze Performance Caused by Lesions Involving the Cholinergic Medial Pathway", Neurosci. 50:129–135.

Mottola, D. et al., 1992, "Dihydrexidine, a Novel Full Efficacy $D_1$ Dopamine Recpetor Agonist", J. Pharmacol. Exp. Ther. 262:383–393.

Mountjoy, C. et al., 1984, "Correlation of Cortical Cholinergic and GABA Deficits with Quantitative Neuropathological Findings in Senile Dementia", Brain 107:507–518.

Murray, C. and Fibiger, H., 1985, "Learning and Memory Deficits After Lesions of the Nucleus Basalis Magnocellularis: Reversal by Physostigmine", Neurosci. 14:1025–1032.

Neill, D. et al., 1974, "Impairment of Avoidance Performance bby Intrastriatal Administration of 6–Hydroxydopamine", Pharmacol. Biochem. Behav. 2:97–103.

Olton, D. and Wenk, G., 1987, "Dementia: Animal Models of the Cognitive Impairments Produced by Degeneration of the Basal Forebrain Cholinergic System", In: *Psychopharmacology: The Third Generation of Progress*, ed.: H. Meltzer, pp. 941–953, Raven Press, New York.

Packard, M. and White, N. 1989, "Memory Facilitation Produced by Dopamine Agonists: Role of Receptor Subtype and Mnemonic Requirements", Pharmacol. Biochem. Behav. 33:511–518.

Packard, M. et al., 1989, "Differential Effects of Fornix and Caudate Nucleus Lesions on Two Radial Maze Tasks: Evidence for Multiple Memory Systems", J. Neurosci. 9:1465–1472.

Packard, M. and White, N., 1990, "Lesions of the Caudate Nucleus Selectively Impair Reference Memory Acquisition in the Radial Maze", Behav. Neural Biol. 53:39–50.

Packard, M. and White, N., 1991, "Dissociation of Hippocampus and Caudate Nucleus Memory Systems by Posttraining Intracerebral Injection of Dopamine Agonists", Behav. Neurosci. 105:295–306.

Perry, R. et al., 1983, "Cortical Cholinergic Deficit in Mentally Impaired Parkinsonian Patients", Lancet ii:789–790.

Phillips, A. and Carr, G., 1987, Cognition and the Basal Ganglia: A Possible Substrate for Procedural Knowledge, Can. J. Neurol. Sci. 14:381–385.

Polgar, S. et al., 1981, "Is the Striatum Involved in Passive–Avoidance Behavior? A Commentary", Physiol. Psychol. 9:354–358.

Rinne, U., 1985, "Combined Bromocriptine–Levodopa Therapy Early in Parkinson's Disease", Neurol. 35:1196–1198.

Robertson, G. et al., 1992, "Lesions of the Mesotelencephalic Dopamine System Enhance the Effects of Selective Dopamine $D_1$ and $D_2$ Receptor Agonists on Striatal Acetylchloine Release", Eur. J. Pharmacol. 219:323–325.

Ruberg, M. et al., 1982, "Muscarinic Binding and Choline Acetyltransferase Activity in Parkinsonian Subjects with Reference to Dementia", Brain Res. 232:129–139.

Santiago, M. et al., 1993, "Regulation of Prefrontal Cortical Dopamine Release by Dopamine Receptor Agonists and Antagonists", Eur. J. Pharmacol. 239:83–91.

Sawaguchi, T. and Goldman–Rakic, P., 1991, "D1 Dopamine Receptors in Prefrontal Cortex: Involvement in Working Memory", Science 251:947–949.

Scatton, B., 1982, "Effect of Dopamine Agonists and Neuroleptic Agents on Striatal Acetylcholine Transmission in the Rat: Evidence Against Dopamine Receptor Multiplicity", J. Pharmacol. Exp. Ther. 220:197–202.

Schneider, J. and Kovelowski II, C., 1990, "Chronic Exposure to Low Doses of MPTP. I. Cognitive Deficits in Motor Asymptomatic Monkeys", Brain Res. 519: 122–128.

Taylor, J. et al., 1991, "Dihydrexidine, a Full Dopamine $D_1$ Agonist, Reduces MPTP–Induced Parkinsonism in Monkeys", Eur. J. pharmacol. 199:389–391.

Vermersch, P. et al., 1993 "Dementia in Parkinson's Disease: Biochemical Evidence for Cortical Involvement Using the Immunodetection of Abnormal Tau Proteins", Ann. Neurol. 33: 445–450.

Whitehouse, P. et al., 1981, "Alzheimer Disease: Evidence for Selective Loss of Choionergic Neurons in the Nucleus Basalis", Ann. Neurol. 10:122–126.

White, N. and Major, R., 1978, "Effect of Pimozide on the Improvement in Learning Produced by Self–Stimulation and by Water Reinforcement", Pharmacol. Biochem. Behav. 8:565–571.

White, N., 1988, "Effect of Nigrostriatal Dopamine Depletion on the Post–Training, Memory–Improving Action of Amphetamine", Life Sci. 43:7–12.

Whitehouse, P. et al., 1982, "Alzheimer's Disease and Senile Dementia: Loss of Neurons in the Basal Forebrain", Science 215:1237–1239.

Whitehouse, P. et al., 1983, "Basal Forebrain Neurons in the Dementia of Parkinson Disease", Ann. Neurol. 13:243–248.

Wilcock, G. et al., 1982, "Alzheimer's Disease", J. Neurol. Sci. 57:407–417.

Wishaw, I. and Dunnet, S., 1985, "Dopamine Depletion, Stimulation or Blockade in the Rat Disrupts Spatial Navigation and Locomotion Dependent upon Beacon or Distal Cues.", Behav. Brain Res. 18:11–29.

Wishaw, I. et al., 1987, "Impairments in the Acquisition, Retention and Selection of Spatial Navigation Strategies After Medical Caudate–Putamen Lesions in Rats", Behav. Brain Res. 24:125–138.

DOPAMINE D₁ AGONISTS FOR THE TREATMENT OF DEMENTIA

FIELD OF THE INVENTION

The present invention is generally directed to a method of treating senile dementia and dementia associated with neurodegenerative diseases (e.g., Parkinson's disease, Alzheimer's disease, etc.) by raising extracellular brain acetylcholine (ACh) levels through the administration of dopamine $D_1$ agonists. A particular embodiment of this invention is directed to the use of trans-10,11-dihydroxy-5,6,6a,7,8,12b-hexahydrobenzo[a]phenanthridine (dihydrexidine; DHX), a dopamine $D_1$ agonist, to raise extracellular brain ACh levels for this purpose.

BACKGROUND OF THE INVENTION

Parkinson's disease (PD) is a disorder of the central nervous system (CNS) that was first described by Dr. James Parkinson in 1817 as "the shaking palsy." PD affects up to 1.5 million Americans (National Parkinson Foundation, *The Parkinson Handbook*). Approximately 1 out of every 100 people over the age of 60 develops the disease; about 5% of patients experience onset before age 40 (ibid). Parkinsonism can be defined as a clinical syndrome consisting of tremor, cogwheel rigidity, bradykinesia, postural instability and gait abnormalities (Koller, Mod Med 57:114–129, 1989). The symptoms of PD begin insidiously, usually on one side of the body, and may slowly worsen. In addition, motor symptoms may be accompanied by dementia or psychological disorders. Estimates of the incidence of dementia vary widely from 20–80% (Brown and Marsden, Lancet ii:1262–1265, 1984). Using established DSM-III criteria, the reported incidence of dementia in PD patient populations ranges from 11–15% (Mayeux et al., J Neurol Neurosurg Psych 51:1498–1502, 1988; Lees, Lancet i:43–44, 1985).

Pathologically, PD is characterized by a reduction in the number of neurons in the substantia nigra which provide dopaminergic innervation to the striatum. There is greater than an 80% depletion of dopamine in the striatum and nearly a total loss of dopamine in the posterior putamen (Kish et al., N Engl J Med 318:876–880, 1988). Less established are the factors contributing to dementia in PD, although cholinergic deficits reminiscent of those found in Alzheimer's disease have been observed (Perry et al., Lancet ii:789–790, 1983; Whitehouse et al., Ann Neurol 13:243–248, 1983; Ruberg et al., Brain Res 232:129–139, 1982).

Pharmacological Treatments of PD

The discovery that PD results from a dopamine deficiency led to the clinical testing of levodopa, the metabolic precursor of dopamine. The introduction of levodopa has allowed PD patients to reach normal life expectancies (Curtis et al., Lancet ii:211–212, 1984). Although levodopa is still considered the primary therapeutic agent for the treatment of PD, it is far from ideal (Goetz, Neurology 40:50–57, 1990). Dopamine agonists have been developed to treat PD in an attempt to avoid many of the limitations of levodopa therapy (ibid). With the recognition of two broad subclasses of dopamine receptors (see Creese, In: *Psychopharmacology: The Third Generation of Progress*, ed. by H. Y. Meltzer, pp. 257–272, Raven Press, New York, 1987 for review), designated $D_1$ and $D_2$, novel dopamine agonists targeted specifically to these receptor subtypes have been developed.

Over the past 15 years, a number of dopamine agonists with selectivity for the dopamine $D_2$ receptor have been tested in the treatment of PD. However, the $D_2$ agonists pergolide and bromocriptine have been shown to have either limited efficacy relative to levodopa or limited long-term efficacy (Goetz, 1990). Current clinical strategy has been to combine the superior efficacy of levodopa with the reduced side effects of the $D_2$ agonists to achieve maximal benefit (i.e., Rinne, Neurology 35:1196–1198, 1985).

The importance of the $D_1$ receptor in the CNS was unclear until the selective $D_1$ antagonist SCH23390 (Iorio et al., J Pharmacol Exp Ther 226:462–468, 1983) became available (Creese, 1987; Mottola et al., J Pharmacol Exp Ther 262:383–393, 1992). SCH23390 was found to mimic some of the behavioral effects previously associated with $D_2$ antagonists (see Creese, 1987). However, functional studies of the $D_1$ receptor have been hampered by the lack of efficacious $D_1$ agonists. For example, the partial $D_1$ agonist, SKF38393, shows greater than 10-fold selectivity for the $D_1$ over the $D_2$ receptor, however, it is only 30–50% as efficacious as dopamine in stimulating adenylate cyclase (Mottola et al., 1992).

Recently, a potent, fully efficacious $D_1$ receptor agonist has been identified (Lovenberg et al., Eur J Pharmacol 166:111–113, 1989; Brewster et al., J Med Chem 33:1756–1764, 1990). Dihydrexidine (DHX) has been reported to have nanomolar affinity and 12- to 60-fold selectivity for the $D_1$ over the $D_2$ receptor (Mottola et al., 1992; Lovenberg et al., 1989). DHX is as efficacious and is approximately 70 times more potent than dopamine in the stimulation of adenylate cyclase (Mottola et al., 1992; Lovenberg et al., 1989; Brewster et al., 1990).

DHX has also demonstrated selectivity and efficacy in vivo (Darney et al., Neuropsychopharmacology 5:187–195, 1991; Taylor et al., Eur J Pharmacol 199:389–391, 1991). In contrast to the partial $D_1$ agonist SKF38393, DHX has shown potent activity in the MPTP-induced parkinsonism model in primates (Taylor et al., 1991). Doses of 0.3 to 0.93 mg/kg of DHX (im) dramatically attenuated parkinsonian signs including tremor, motor freezing, abnormal posture, rigidity, and bradykinesia, while increasing eye blink rates (Taylor et al., 1991). These results clearly establish a critical role for $D_1$ receptor occupancy in the attenuation of parkinsonian signs.

Dementia in Alzheimer's and Parkinson's Diseases

In recent years, extensive attention has focused on cholinergic deficits in dementia (Olton and Wenk, In: *Psychopharmacology: The Third Generation of Progress*, ed. by H. Y. Meltzer, pp. 941–953, Raven Press, New York, 1987). It is well established that intellectual impairment in Alzheimers disease (AD) is associated with a loss of cholinergic presynaptic markers in cortex and hippocampus (Arendt et al., Neuroscience 14:1–14, 1985; Mountjoy et al., Brain 107:507–518, 1984; Whitehouse et al., Ann Neurol 10:122–126, 1981) and pathological changes in the basal forebrain (Whitehouse et al., Science 215:1237–1239, 1982; Wilcock et al., J Neurol Sci 57:407–417, 1982). The treatment of dementia with acetylcholinesterase inhibitors, which elevate synaptic concentrations of ACh by preventing its degradation, is consistent with this scheme. Conversely, anticholinergic drugs frequently cause memory impairments (Bianchine, In: *The Pharmacological Basis of Therapeutics*, ed. by A. G. Gilman, L. S. Goodman, T. W. Rall and F. Murad, pp. 473–490, Macmillan Publishing Co., New York, 1985).

Dementia is also associated with PD. Neural pathologies similar to those of AD have been reported in patients with PD including loss of choline acetyltransferase activity (Perry et al., 1983) and cell loss in the nucleus basalis of Meynert (Whitehouse et al., 1983). These similar pathologies have made difficult the distinction between dementia of PD or coexisting conditions of PD and AD.

The characteristics of intellectual changes in dementia of PD are indicative of subcortical deficits (impaired recall, visuospatial disturbances, executive deficits, bradyphrenia and depression). However, decreased dopamine levels in neocortical areas are greater in demented than non-demented patients suggesting that degeneration of mesocortical dopaminergic neurons could also contribute to intellectual impairments in PD patients (Dubois et al. J Neurol 239 Suppl 1:S9–12, 1992). Similarly, a recent study has indicated the presence of AD-like changes in the cortex of demented PD patients (Vermersch et al., Ann Neurol 33:445–450, 1993). Heterogeneous conditions of dementia associated with PD may be the products of dopamine deficiency, combined dopaminergic and cholinergic deficiencies, and combined AD and PD (Cummings Eur. Neurol. 28 Suppl 1:15–23, 1988).

Animal Models of Learning and Memory

Because of its relevance to AD, the cholinergic system of the basal nuclear complex (medial septal nucleus, diagonal band and the nucleus basalis) has received considerable attention. Lesions of the projections of this complex to defined regions of the cortex impair learning and memory in a variety of tasks (Murray and Fibiger, Neuroscience 14:1025–1032, 1985; Bartus et al., Pharmacol Biochem Behav 23:125–135, 1985; Dubois et al., Brain Res 338:249–258, 1985). The memory-disrupting effects of these types of lesions can be reversed by the administration of cholinergic agonists (Murray and Fibiger, 1985; Dunnett, Psychopharmacology 87:357–363, 1985).

Modulation of dopaminergic systems has also been found to affect learning and memory. It has been reported in numerous studies that alterations in learning and memory occur after stimulation or lesioning of the striatum. Phillips and Carr (Can J Neurol Sci 14:381–385, 1987) noted that animals with caudate lesions are impaired in tasks that require a consistent choice of direction or the consistent choice to initiate or withhold responses indicating that damage to the basal ganglia may be responsible for selective impairments of procedural learning. Experimentally, these deficits translate to impairments in "reference memory" aspects of the radial arm maze (Packard et al., J Neurosci 9:1465–1472, 1989; Packard and White, Behav Neural Biol 53:39–50, 1990; Colombo et al., Behav Neurosci 103:1242–1250, 1989), active (Kirby and Polgar, Physiol Psychol 2:301–306, 1974) and passive avoidance (Packard and White, Behav Neurosci 105:295–306, 1991; Polgar et al., Physiol Psychol 9:354–358, 1981), Morris water maze (Wishaw et al., Behav Brain Res 24:125–138, 1987) and split-T maze (Colombo et al., 1989). Lesions of the nigrostriatal tract with 6-hydroxydopamine (6-OHDA) impair a variety of learning tasks including avoidance conditioning (Neill et al., Pharmacol Biochem Behav 2:97–103, 1974) and Morris water maze (Wishaw and Dunnett, Behav Brain Res 18:11–29, 1985; Archer et al., Pharmacol Biochem Behav 31:357–64, 1988). Post-training self-stimulation of the nigrostriatal tract improves memory (Major and White, Physiol Behav 20:723–733, 1978) and the effect can be blocked with the dopamine antagonist pimozide (White and Major, Pharmacol Biochem Behav 8:565–571, 1978). The indirect dopamine agonist d-amphetamine has exhibited memory-improving effects in a number of studies (McGaugh, Science 153:1351–1358, 1966; White, Life Sci 43:7–12, 1988), which can be blocked by 6-OHDA (White, 1988).

Less clear is the role of individual dopamine receptor subtypes on learning and memory performance in rodents. In win-stay (sensitive to caudate lesions) and win-shift (sensitive to fornix/hippocampal lesions) paradigms, d-amphetamine, selective $D_2$ agonists, but not SKF38393, improved retention of the tasks leading to the conclusion that the effects of dopamine on memory were facilitated by the $D_2$ subtype (Packard and White, Pharmacol Biochem Behav 33:511–8, 1989). However, in a subsequent study, these investigators found that post-training intracaudate injection of either d-amphetamine, $D_1$ or $D_2$ agonists improved win-stay acquisition, but intrahippocampal injections of the dopamine agonists were ineffective in the win-stay task. Conversely, intrahippocampal, but not intracaudate, injections of dopamine agonists improved the win-shift task. These results suggest that dopamine receptor activation improves memory processes in both the caudate and hippocampus (Packard and White, 1991). Similarly, both $D_1$ and $D_2$ agonists have been shown to facilitate and antagonists impair retention of an inhibitory avoidance response (Castellano et al., Behav Neural Biol 56:283–91, 1991). In a radial arm maze model, SKF38393, but not quinpirole, alleviated choice accuracy deficits (CADS) due to scopolamine (Levin and Rose, Pharmacol Biochem Behav 38:243–246, 1991). Both the $D_1$ and $D_2$ agonists and the D1 antagonist SCH23390 reversed CADs due to lesions of the medial projection of the basal forebrain to the cortex (McGurk et al., Neuroscience 50:129–35, 1992).

As in Parkinsonian patients, primates with lesions of dopaminergic neurons exhibit difficulty in performing procedural cognitive tasks. Cognitive deficits have been reported in monkeys depleted of dopamine in the prefrontal cortex (Brozoski et al., Science 205:929–932, 1979), and in asymptomatic MPTP-treated primates (Schneider and Kovelowski, Brain Res 519:122–128, 1990). Local injection of $D_1$ antagonists into the prefrontal cortex of monkeys induced errors and increased latency in performance of a task requiring memory guided saccades suggesting a significant role for the $D_1$ receptor in mnemonic, predictive function of the primate prefrontal cortex (Sawaguchi and Goldman-Rakic, Science 251:947–949, 1991). Consistent with this interpretation are the observations of Arnsten et al. (Neurosci Abst 19:367, 1993). Administration of the partial $D_1$ agonist SKF 38393 improved spatial working memory in aged and reserpine-treated monkeys; the full $D_1$ agonist DHX produced improvements in young, intact monkeys.

Doyamine receptor activation and ACh release

In contrast to previously held notions that dopamine is solely inhibitory on striatal cholinergic mechanisms (Calne, Postgrad Med 64:82–88, 1978; Scatton, J Pharmacol Exp Ther 220:197–202, 1982), in vivo microdialysis techniques have demonstrated divergent effects of dopamine receptor subtypes on ACh release in the striatum (Robertson et al., Eur J Pharmacol 219:323–325, 1992; Scatton, 1982). Stimulation of $D_2$ receptors, presumably located on cholinergic interneurons in the striatum, decreases extracellular concentrations of ACh (Bertorelli and Consolo, J Neurochem 54:2145–2148, 1990; Damsma et al., Naunyn-Schmiedeberg's Arch Pharmacol 342:523–527, 1990; Scatton, 1982). In contrast, systemic administration of the $D_1$ agonists (+)-SKF 38393 and CY204–283 have been shown to increase striatal ACh output by 75% (Damsma et al., Eur J Pharmacol 186:335–338, 1990). This effect was blocked by the $D_1$ antagonist SCH 23390 (0.3 mg/kg) and potentiated by the D2 antagonist raclopride administered 60 min after SKF 38393.

$D_1$ receptors have also been implicated in the release of ACh in the cortex and hippocampus. ACh is released in the cortex primarily from the terminals of projections from the nucleus basalis of Meynert. The $D_1$ agonist CY 208–243 significantly increased cortical ACh release, whereas the $D_2$ agonists quinpirole and PHNO had no effect (Day and Fibiger, Neurosci 54:643–648, 1993). The $D_1$ agonist-induced increase in cortical ACh release was blocked selectively by SCH 23390. In the hippocampus, both $D_1$ and $D_2$ agonists have been found to increase ACh release (Imperato et al., Brain Res 618:341–345, 1993). Although independent lines of evidence have demonstrated that $D_1$ receptor agonists are able to elevate ACh release in brain areas relevant to cognition, and reverse learning deficits generally associated with decreases in cholinergic neurotransmission, a link between the two phenomena has not been completely investigated or elucidated. The existence of such a link has been postulated within the context of a discussion in a manuscript describing the ACh-releasing properties of dopamine receptor agonists in rat hippocampus (Imperato et al., 1993).

Therapeutic Approaches to Dementia

A number of strategies have been used to restore cognitive function in AD, primarily focusing on increasing cholinergic neurotransmission via the administration of precursors to ACh (e.g., choline, lecithin) to increase endogenous ACh stores available for release, the administration of acetylcholinesterase inhibitors (e.g., physostigmine) to prevent the synaptic degradation of ACh, the administration of cholinergic receptor agonists (i.e., arecoline, oxotremorine) to stimulate postsynaptic receptors directly and the administration of transmitter releasing agents (i.e., 4-aminopyridine) to augment the release of neuronal ACh (Davidson et 0al. Acta Psychiatr Scand, Suppl 366:47–57, 1991). Unfortunately, these approaches have to date yielded only marginally successful clinical treatments for AD. The therapeutic potential of most of the drugs that have been tested have been limited by factors such as a short duration of action, a lack of specificity, poor penetration into the central nervous system (CNS), significant peripheral side effects and/or a small therapeutic index (Davidson et al., 1991).

BRIEF SUMMARY OF THE INVENTION

The present invention is generally directed to a method of raising extracellular brain ACh levels by the administration of dopamine $D_1$ agonists for the treatment of senile dementia and dementia associated with neurodegenerative diseases (e.g., PD, AD, etc.).

For example, the present method is applicable to dementia associated with the following clinical conditions: Parkinson's disease, Alzheimer's disease, HIV disease, head trauma, Huntington's disease, Pick's disease, Creutzfeldt-Jakob disease and stroke.

Dopamine $D_1$ agonists can be defined as chemical entities with at least micromolar affinity for $D_1$ receptors as determined by radioligand binding experiments and that are positively coupled to adenylate cyclase. Increases in brain levels of ACh can be defined more specifically as statistically significant increases (relative to basal release) in the ACh release into the extraneuronal space following the administration of a $D_1$ agonist, as measured by in vivo microdialysis or by essentially equivalent techniques. These increases in ACh release should occur in at least one area of the brain relevant to cognition (e.g., striatum, hippocampus, frontal cortex). The dopamine $D_1$ agonist may be administered in conjunction with an effective amount of levodopa, dopamine $D_2$ agonist, monoamine oxidase inhibitor, acetylcholinesterase inhibitor, apomorphine or muscarinic $m_1$ agonist or a mixture thereof.

A particular embodiment of this invention is directed to the use of dihydrexidine, a dopamine $D_1$ agonist, to raise extracellular brain acetylcholine levels for the treatment of dementia. The term dihydrexidine is meant to include its racemic mixture, its (+) optical isomer and its (−) optical isomer. For parenteral administration of DHX (e.g. intravenous, intramuscular and subcutaneous), as well as intranasal, sublingual and transdermal administration of DHX, the preferred dosage range is from about 0.1 to about 10 mg/kg, and the most preferred dosage range is from about 0.3 to about 3 mg/kg. For oral administration of DHX, the preferred dosage range is from about 0.1 to about 100 mg/kg, and the most preferred dosage range is from about 0.3 to 30 mg/kg.

A variety of pharmaceutical vehicles may be used in conjunction with DHX to form the appropriate pharmaceutical composition. Such vehicles are chosen, in part, to enhance the stability of DHX and to facilitate the delivery of DHX or its metabolite(s) to the brain.

Examples of the present invention are presented below. Passive avoidance experiments provide functional evidence of the utility of the invention by demonstrating a reversal of learning deficits in an animal model of dementia. The proposed neurochemical basis of this action is demonstrated using in vivo microdialysis experiments showing an elevation of ACh levels by $D_1$ dopamine agonists in brain regions relevant to cognition.

DETAILED DESCRIPTION OF THE INVENTION

Passive Avoidance in Rats

The protocol summarized below is one of many variants of the passive avoidance procedure using scopolamine-induced amnesia (for review see Rush, Behav Neural Biol 50:255–274, 1988). This procedure is commonly used to identify drugs that may be useful in treating cognitive deficits, particularly those observed in AD. The effects of the $D_1$ agonist DHX in this assay were evaluated to demonstrate the potential of this class of drugs to treat dementia.

Testing was conducted in standard 2-compartment rectangular passive avoidance chambers (San Diego Instruments, San Diego, Calif.) with black plexiglas sides and grid floors. The light compartment of the chambers were illuminated by a 20 W lamp located in this compartment; the dark side of the chambers will be shielded from light, except for light penetrating the opening connecting the two compartments of each chamber.

On training day, groups of 8 rats were injected with scopolamine (3.0 mg/kg, ip) or vehicle (1.0 ml/kg) 30 min prior to training. Scopolamine served as the dementing agent in this experiment. Ten min prior to training, each group of rats received a second injection of vehicle or a dose of DHX. At the end of the pretreatment interval, each rat was placed individually in the light compartment facing away from the opening between compartments. The latency for each rat to travel from the light to the dark compartment was measured up to a maximum of 300 sec; any animal not entering the dark compartment within 300 sec was discarded from the test group. Once the animal entered the dark compartment completely, a 1.0 milliampere, 3.0 sec scrambled shock was delivered to the entire grid floor. The animal was allowed to remain in the dark compartment during this 3.0 sec period or to escape to the light compartment. Each rat was then returned immediately to its home cage.

Twenty-four hr after training, each rat was tested in the same apparatus for retention of the task (to remain passively in the light compartment). The procedure on test day was identical to that of the training day, except that no injections were given and that the rats did not receive a shock upon entering the dark compartment. The latency for animals to enter the dark compartment on test day (step-through latency) was recorded up to a maximum of 600 sec. Each animal was used only once in a single experiment.

A one-way analysis of variance (ANOVA) and Newman-Keuls post-hoc comparisons were used to identify significant deficits in passive avoidance responding produced by scopolamine and their reversal by DHX; a p value of less than 0.05 was used as the level of significance.

Figure 1:
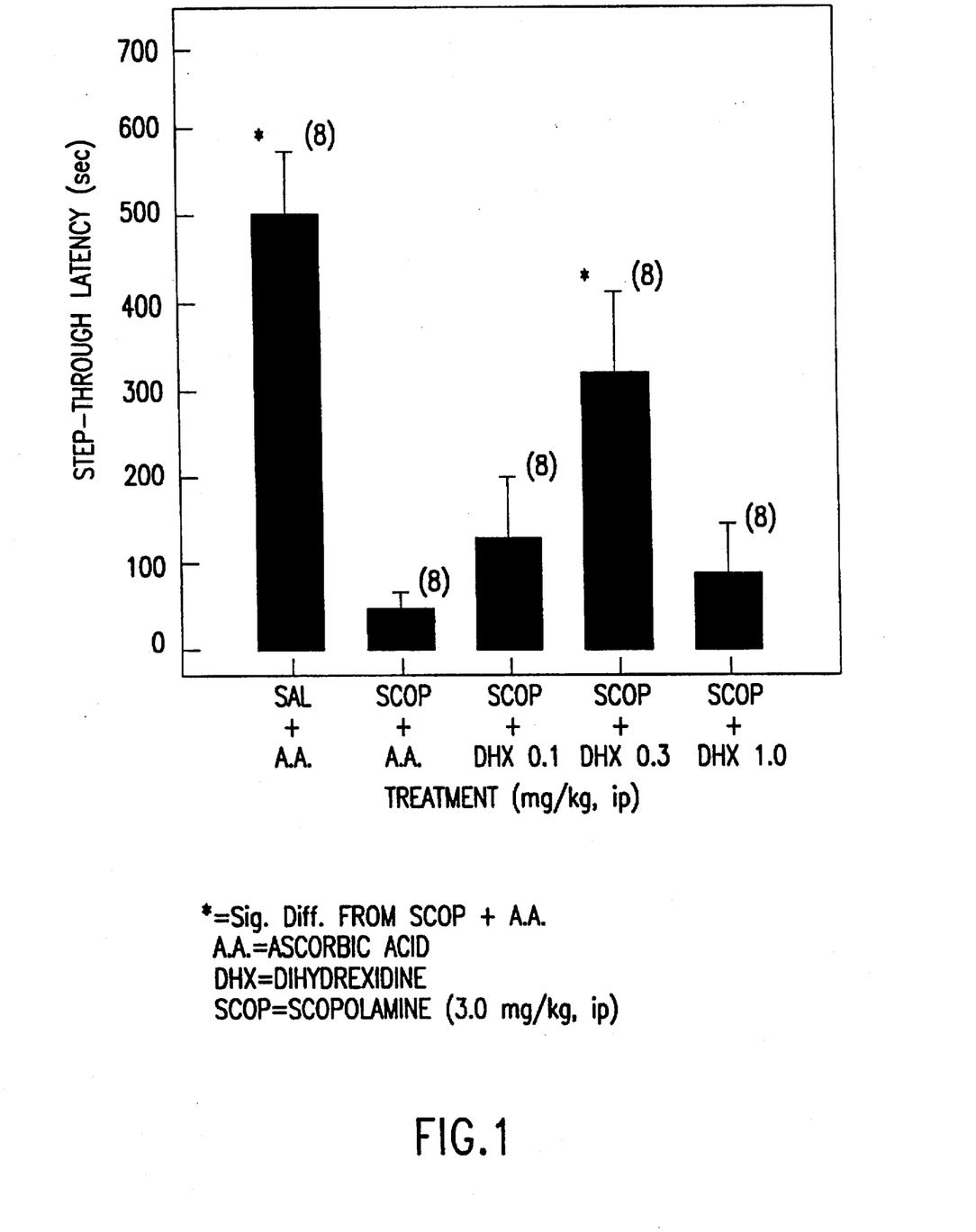
FIG. 1 shows the results of a passive avoidance protocol. Administration of 0.3 mg/kg of DHX significantly improve scopolamine-induced deficits.

Scopolamine (3.0 mg/kg) produced a severe deficit in the acquisition of the passive avoidance task. DHX significantly improved scopolamine-induced deficits in step-through latency at a dose of 0.3 mg/kg (FIG. 1). Doses of 0.1 and 1.0 mg/kg of DHX also increased step-through latency, however, these increases were not statistically-significant. These results are similar to those obtained with drugs such as physostigmine which have been used in the treatment of AD. These results are also consistent with the hypothesis that dopamine $D_1$ agonists may be effective in the treatment of dementia.

In vivo microdialysis

The in vivo microdialysis technique is a method for evaluating the effects of drugs on brain neurotransmitter systems by monitoring the extracellular concentration of neurotransmitters and metabolites in awake freely-moving animals. Probes are implanted directly into the brain of rats and serve to continuously sample the extracellular fluid in the vicinity of the probe. Samples containing the dialyzed extracellular fluid are collected at the outlet of the perfusion system and analyzed for content of brain neurotransmitters and metabolites by high-performance liquid chromatography coupled with electrochemical detection (HPLC-EC).

Male Sprague-Dawley rats weighing 250–350 g were group housed (n=3 per cage) in a temperature-controlled room (23±2° C.) on a 14/10 hr light cycle with free access to food and water. After the surgical procedure, animals were placed in individual cages.

The surgical procedure involved the implantation and fixation of a probe holder/guide cannula to the skull of anesthetized rats. The guide cannula was the attachment site for the rigid concentric microdialysis probes which were implanted into the awake, fully-recovered rat at the onset of the experiment. Guide cannulae were of either the "non-penetrating" type (those that do not extend below dura into the brain), or the "penetrating" type (those that penetrate the dura and extend into brain tissue). For placement of the guide cannulae, rats were anesthetized with ketamine:xylazine (87:13 mg/kg), shaved and placed in a stereotaxic frame (Narashige Instruments). An incision was made to expose the skull and a small hole was drilled to expose the dura mater for placement of the guide. Guide cannulae were implanted in the striatum according to the following stereotaxic coordinates with reference to bregma: AP —+1.5 mm, L —+2.6 mm and V to dura −2.5 mm (Paxinos and Watson, *The rat brain in stereotaxic coordinates*, 2nd. ed., Academic Press, London, 1986). The microdialysis probe extended 3.0 mm beyond the tip of the guide cannula which yielded a final ventral placement of 5.5 mm below the dura. The coordinates for placement of the guide into frontal cortex were: AP —+3.0 mm, L —+2.8 mm and V to dura 0 mm, with the probe extending 3.0 mm below the dura. Guide cannulae were fixed to the skull with dental acrylic and anchor screws and a dummy cannula was inserted into each guide for the recovery period. Animals were returned to their home cage and allowed to recover from surgery for 24–48 hrs.

For each experiment, the dialysis probe was connected to a microinfusion pump (CMA-100; Bioanalytical Systems (BAS); W. Lafayette, Ind.) equipped with a liquid switch (CMA-110; BAS) via low dead volume fused-silica tubing (I.D.=75 um; O.D.=150 um). At the time of experiment, the dummy cannula was removed and the probe was inserted through the guide into the conscious animal under light restraint. Animals subjected to this procedure displayed minimal signs of discomfort upon probe insertion.

The probe was perfused continuously with artificial CSF (composition in Mm: 121 NaCl, 3.5 KCl, 1.2 $CaCl_2$, 1.2 $MgCl_2$, 1.0 $NaH_2PO_4$, 25 $NaHCO_3$, and 0.001 neostigmine) at a flow rate of 1.5 ul/min. Dialysate samples were collected every 20 min (total sample volume=30 µl). A 20 ul aliquot was analyzed immediately for acetylcholine (ACh) content by high-performance liquid chromatography with electrochemical detection (HPLC-EC) (see below for details). A baseline period of at least one hour was allowed prior to invoking any experimental manipulations. The established criteria for determining basal ACh release was the collection of three consecutive samples which did not vary in ACh content by more than 10%. Sample collection proceeded for a minimum of 3 hrs following drug administration. Upon completion of the experiment, animals were sacrificed by decapitation and brains examined grossly to verify probe placement.

DHX and SKF 81297, another $D_1$ agonist (Andersen et al., Eur J Pharmacol 188:335, 1990), were administered ip after a stable baseline of ACh release was established in each animal. To verify that the effects observed following the injection of DHX were due to stimulation of $D_1$ receptors, experiments were conducted with DHX in combination with low doses of the $D_1$ antagonist SCH23390. The effects of DHX on ACh release were evaluated in two brain regions associated with cognition (striatum, frontal cortex).

The HPLC-EC instrumentation for the analysis of ACh consisted of components from Bioanalytical Sytems/Carnegie-Mellon (BAS/CMA, West Lafayette, Ind.) including a CMA-200 refrigerated microsampler, a PM-60 pump, and an LC-4C amperometric detector. The mobile phase for the chromatographic separation was 35 Mm $Na_2HPO_4$ (Ph 8.5) containing 0.005% Kathon as an antibacterial agent delivered at a flow rate of 1 ml/min. ACh was isolated in samples using an analytical column equipped with a post-column reactor containing the immobilized enzymes acetylcholinesterase and choline oxidase (BAS). The enzymes convert ACh, which is not significantly electrochemically reactive, to hydrogen peroxide ($H_2O_2$). The $H_2O_2$ product of the enzyme reactor is detected by oxidation with a platinum electrode at a potential of +500 mV versus a Ag/AgCl reference electrode. Output from the detector was recorded on a chart recorder. Peak heights were measured manually and converted to pmol/injection by interpolation on a standard curve.

Figure 2:
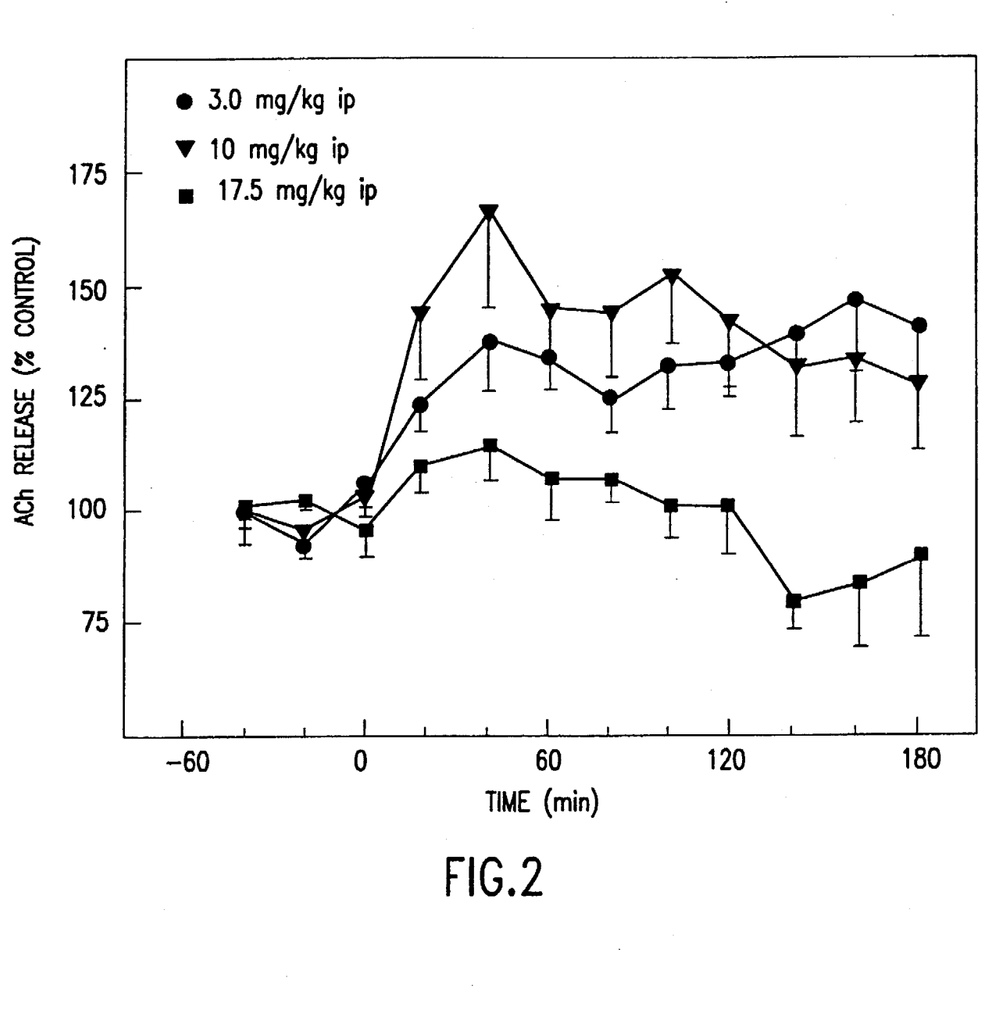
FIG. 2 shows an increase in dialysate concentration of striatal acetylcholine upon i.p. administration of 3.0 and 10 mg/kg of DHX.
Figure 3:
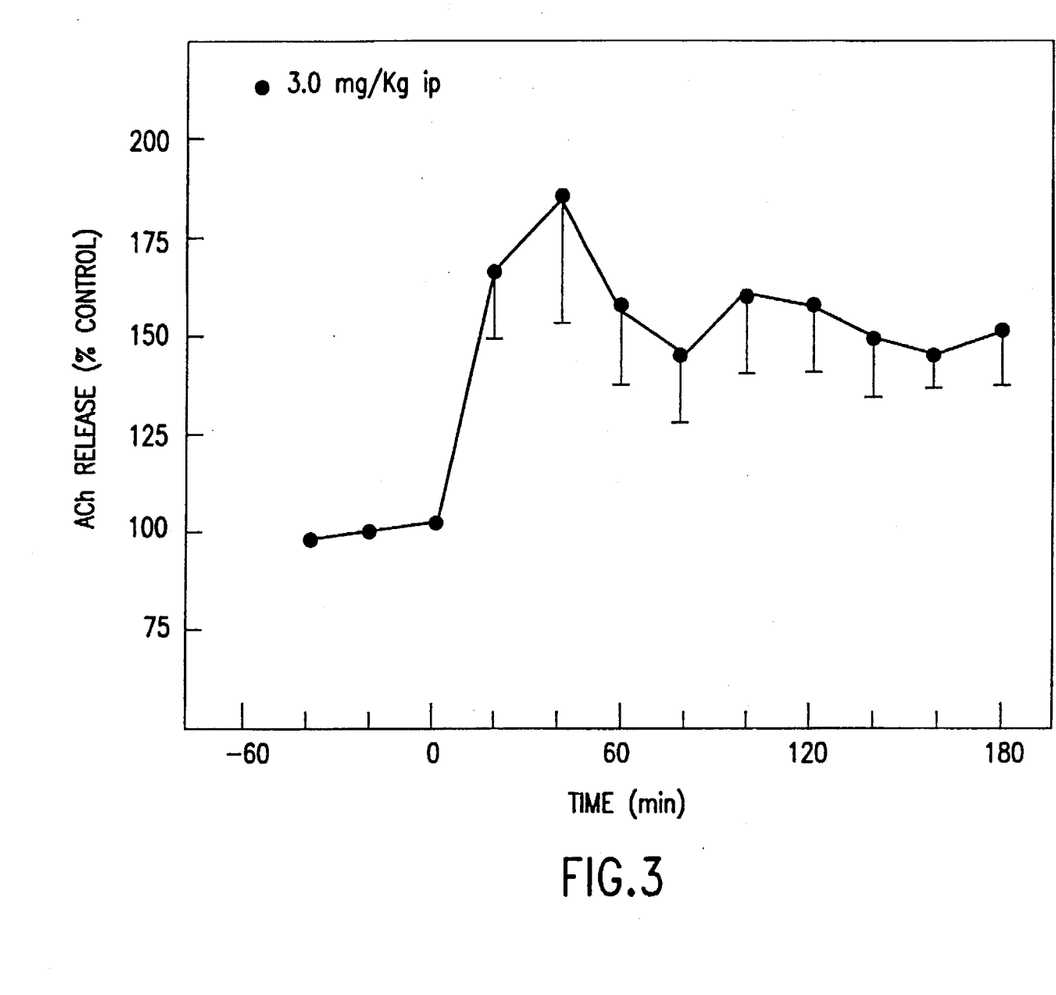
FIG. 3 shows an increase in dialysate concentration of striatal acetylcholine upon i.p. administration of 3.0 mg/kg of SKF 81297.
Figure 4:
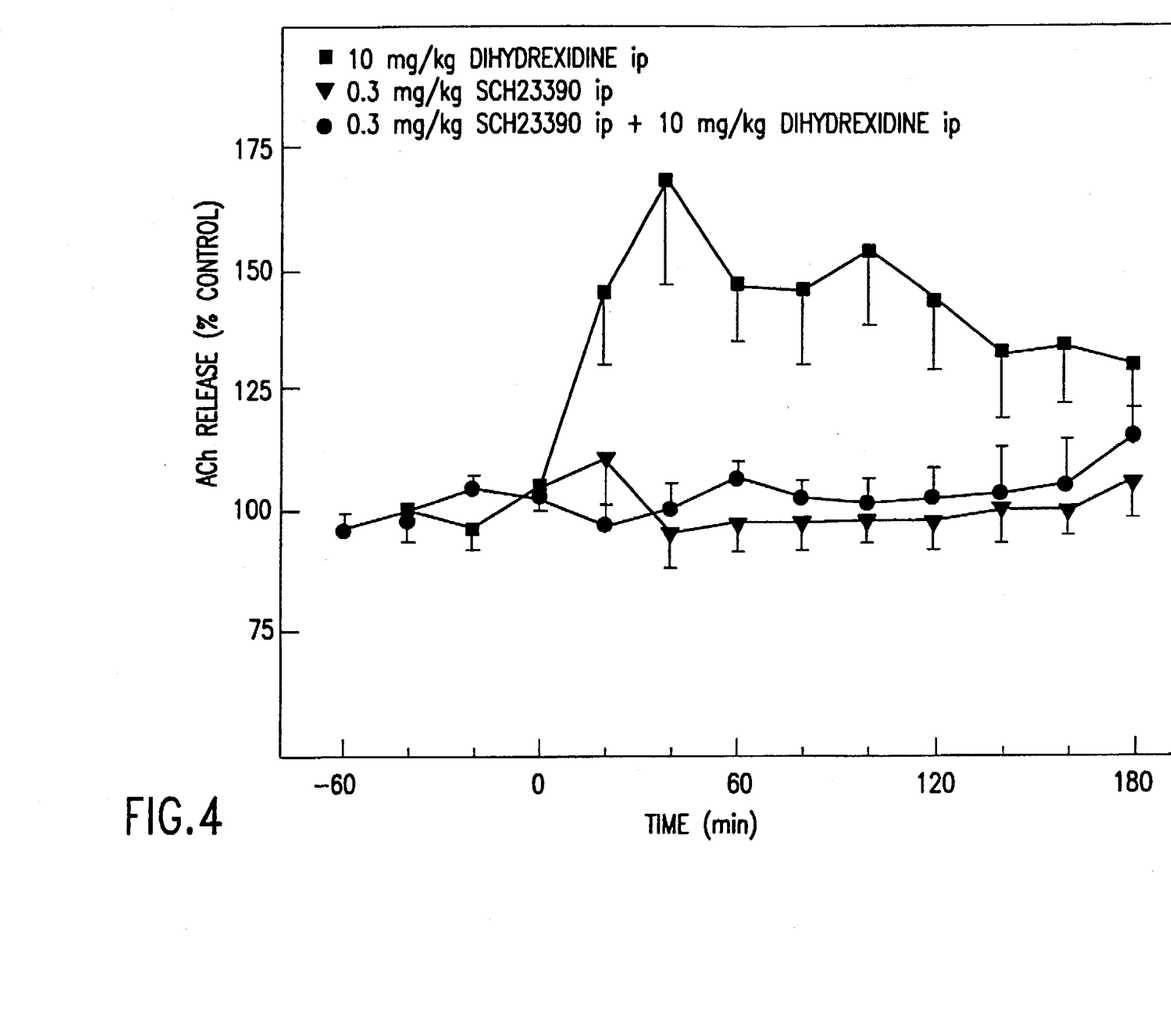
FIG. 4 shows the ability of SCH 23390, a known $D_1$ antagonist, to completely block the stimulatory effect of administering DHX on striatal acetylcholine release.
Figure 5:
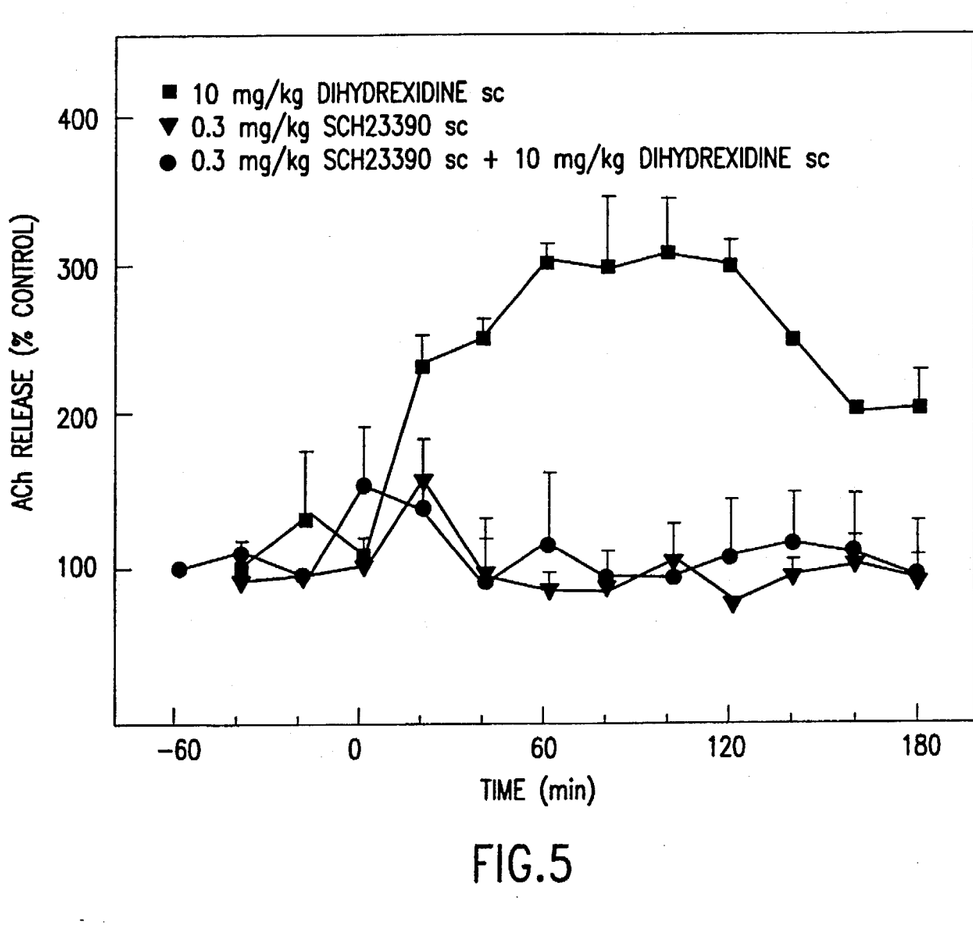
FIG. 5 shows an increase in acetylcholine release in the frontal cortex upon the injection of DHX. It also shows the ability of SCH 23390, a known $D_1$ antagonist, to completely block the stimulatory effect of administering DHX on acetylcholine release in the frontal cortex.

The results of these experiments show that relatively low doses of DHX (3.0 and 10 mg/kg, i.p.) increase dialysate concentrations of striatal ACh for at least 180 min post-injection (FIG. 2). ACh release in response to a higher dose of DHX (17.5 mg/kg) appears to be less than that evoked by lower doses. This may reflect $D_2$-mediated events (i.e. inhibition of ACh release) due to the loss of receptor selectivity at higher doses. Support for this hypothesis comes from the finding that the $D_2$ agonist quinpirole (2.0 mg/kg) decreases striatal ACh release (data not shown). A relatively low dose of SKF 81297 (3.0 mg/kg) also elevated striatal ACh release (FIG. 3). This suggests that the stimulation of striatal ACh release may be a common property of $D_1$ agonists. The ability of the $D_1$ antagonist SCH23390 to completely block the stimulatory effect of DHX on striatal ACh release further confirms that this effect was $D_1$-mediated (FIG. 4). The generality of the findings to other areas of the brain was examined. As in the striatum, DHX increased ACh release in the frontal cortex (FIG. 5). This effect was again sensitive to antagonism by SCH 23390. These results suggest that $D_1$ agonists such as DHX elevate ACh concentrations in areas of the brain relevant to cognition through an interaction with $D_1$ receptors.

Figure 6A:
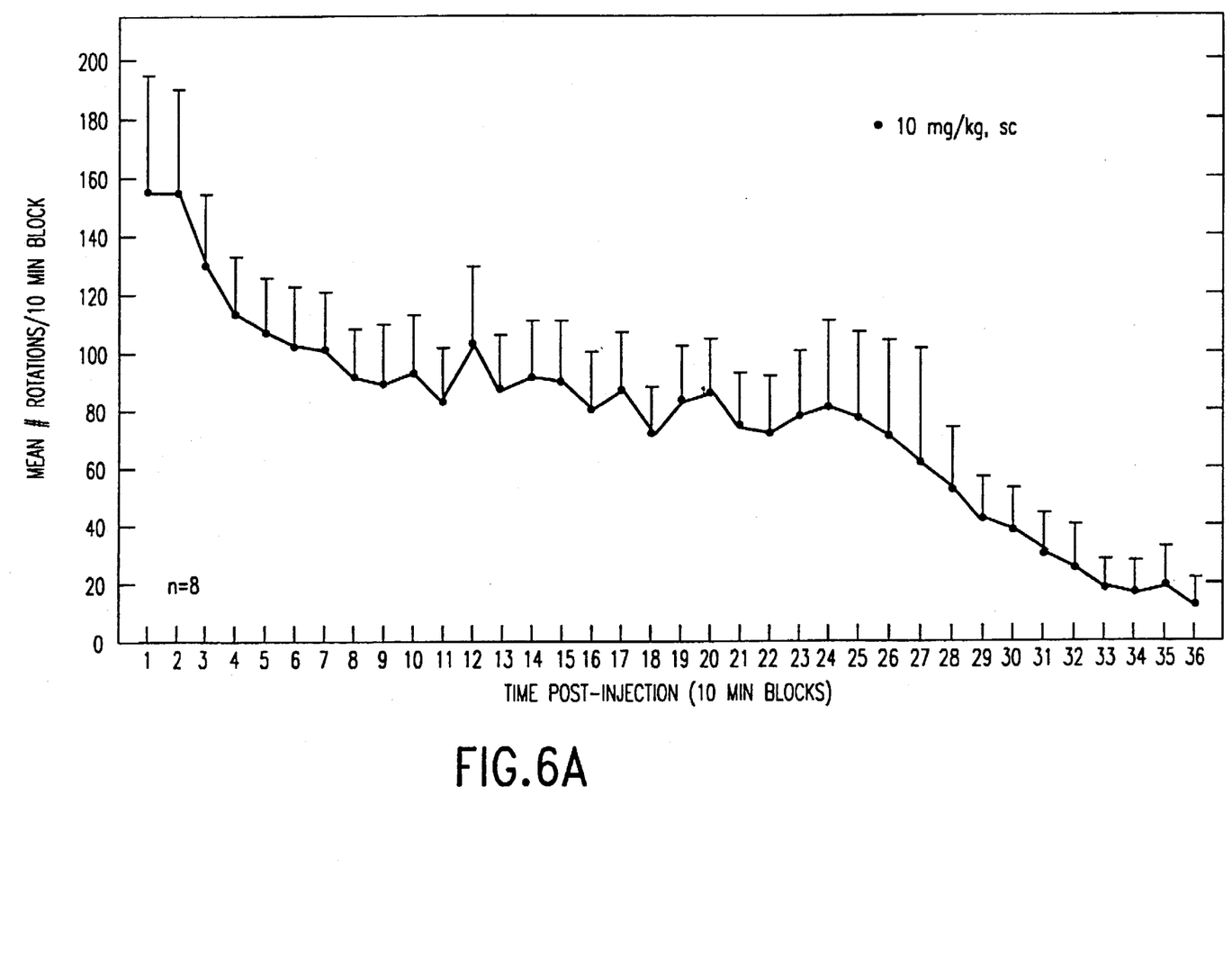
FIG. 6A shows the rotational behavior in 6-OHDA-lesioned rats over time after the injection of 10 mg/kg of DHX.
Figure 6B:
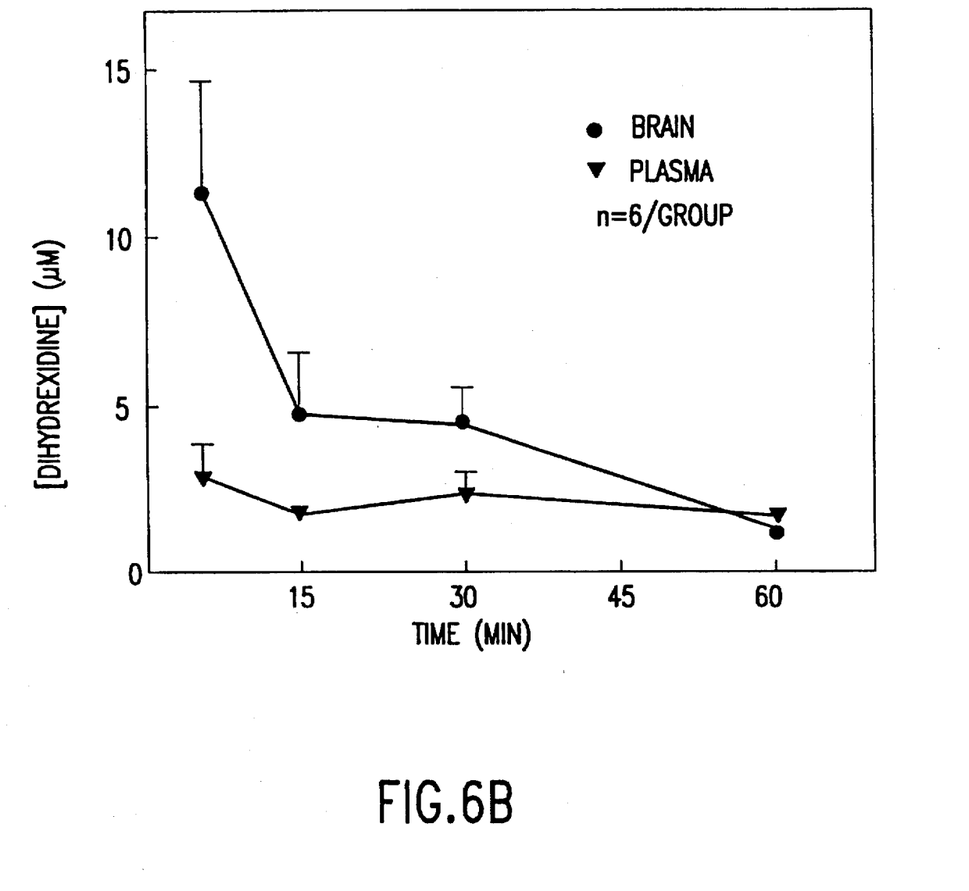
FIG. 6B shows the concentration of DHX in the brain and plasma over time after the injection of 10 mg/kg of DHX.

Further, biological activity of 10 mg/kg of DHX in a rodent model of PD (FIG. 6A) persists long after the levels of DHX in the brain and plasma have diminished (FIG. 6B). The test protocol followed is disclosed in Ungerstedt, Acta Physiol. Scand. 82 Supp. 367, p. 49–68 (1971). These data indicate that DHX may have at least one metabolite of significant biological activity. This activity may reside in one or more optical isomers of such a metabolite.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims.

All references cited in the present application are incorporated by reference in their entirety.

What is claimed:

1. A method of raising extracellular brain acetylcholine levels to improve cognition in a human having senile or presenile dementia associated with neurodegeneration which comprises administering to said human in need of such treatment an effective amount of dihydrexidine, said effective amount being from about 0.1 to about 10 mg/kg.

2. The method of claim 1 wherein the neurodegeneration is associated with a clinical condition selected from the group consisting of Parkinson's disease, Alzheimer's disease, HIV disease, head trauma, Huntington's disease, Pick's disease, Creutzfeldt-Jakob disease and stroke.

3. The method of claim 1 wherein the pharmaceutical composition further comprises an effective amount of levodopa, dopamine $D_2$ agonist, monoamine oxidase inhibitor, acetylcholinesterase inhibitor, apomorphine, muscarinic $m_1$ agonist, or a mixture thereof.

4. The method of claim 1 wherein the pharmaceutical composition is administered intravenously, intramuscularly, subcutaneously, intranasally, sublingually or transdermally.

5. The method of claim 4 wherein the dosage range of dihydrexidine is about 0.1 to about 10 mg/kg.

6. The method of claim 5 wherein the dosage range of dihydrexidine is about 0.3 to about 3 mg/kg.

7. The method of claim 1 wherein the pharmaceutical composition is administered orally.

8. The method of claim 7 wherein the dosage range of dihydrexidine is about 0.1 to about 100 mg/kg.

9. The method of claim 8 wherein the dosage range of dihydrexidine is about 0.3 to about 30 mg/kg.

10. A method of raising extracellular brain acetylcholine levels to improve cognition in a human having senile or presenile dementia associated with neurodegeneration which comprises administering to said human in need of such treatment an effective amount of the (+) optical isomer of dihydrexidine, said effective amount being from about 0.1 to about 10 mg/kg.

11. The method of claim 10 wherein the neurodegeneration is associated with a clinical condition selected from the group consisting of Parkinson's disease, Alzheimer's disease, HIV disease, head trauma, Huntington's disease, Pick's disease, Creutzfeldt-Jakob disease and stroke.

12. The method of claim 10 wherein the pharmaceutical composition further comprises an effective amount of levodopa, dopamine $D_2$ agonist, monoamine oxidase inhibitor, acetylcholinesterase inhibitor, apomorphine, muscarinic $m_1$ agonist or a mixture thereof.

13. The method of claim 10 wherein the pharmaceutical composition is administered intravenously, intramuscularly, subcutaneously, intranasally, sublingually or transdermally.

14. The method of claim 13 wherein the dosage range of the (+) optical isomer of dihydrexidine is about 0.1 to about 10 mg/kg.

15. The method of claim 14 wherein the dosage range of the (+) optical isomer of dihydrexidine is about 0.3 to about 3 mg/kg.

16. The method of claim 10 wherein the pharmaceutical composition is administered orally.

17. The method of claim 16 wherein the dosage range of the (+) optical isomer of dihydrexidine is about 0.1 to about 100 mg/kg.

18. The method of claim 17 wherein the dosage range of the (+) optical isomer of dihydrexidine is about 0.3 to about 30 mg/kg.

* * * * *